United States Patent
Ushifusa

(10) Patent No.: US 8,566,052 B2
(45) Date of Patent: Oct. 22, 2013

(54) PROBE SHAPE DETECTION APPARATUS AND PROBE SHAPE DETECTION METHOD

(75) Inventor: Hiroyuki Ushifusa, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/596,524

(22) Filed: Aug. 28, 2012

(65) Prior Publication Data

US 2013/0054168 A1 Feb. 28, 2013

Related U.S. Application Data

(63) Continuation of application No. PCT/JP2011/062685, filed on Jun. 2, 2011.

(30) Foreign Application Priority Data

Jun. 9, 2010 (JP) ................. 2010-132211

(51) Int. Cl.
- G01R 25/00 (2006.01)
- G01R 27/00 (2006.01)
- G01C 9/00 (2006.01)
- G01C 17/00 (2006.01)
- G01C 19/00 (2013.01)
- A61B 5/05 (2006.01)

(52) U.S. Cl.
USPC .............................. 702/65; 600/424; 702/150

(58) Field of Classification Search
USPC .................... 702/65, 150; 600/424
See application file for complete search history.

(56) References Cited

U.S. PATENT DOCUMENTS

| | | | |
|---|---|---|---|
| 2002/0188174 A1* | 12/2002 | Aizawa et al. | 600/118 |
| 2007/0219410 A1 | 9/2007 | Onoda et al. | |
| 2007/0232854 A1 | 10/2007 | Miyake et al. | |
| 2007/0238922 A1* | 10/2007 | Oda et al. | 600/117 |
| 2010/0016666 A1* | 1/2010 | Hasegawa | 600/118 |

FOREIGN PATENT DOCUMENTS

| | | |
|---|---|---|
| EP | 1 813 183 A1 | 8/2007 |
| EP | 1 818 004 A1 | 8/2007 |

(Continued)

OTHER PUBLICATIONS

International Search Report dated Jul. 12, 2011 issued in PCT/JP2011/062685.

*Primary Examiner* — Alexander H Taningco
*Assistant Examiner* — Manuel Rivera Vargas
(74) *Attorney, Agent, or Firm* — Scully, Scott, Murphy & Presser, P.C.

(57) ABSTRACT

A probe shape detection apparatus includes first and second magnetic field detection sections that outputs a signal in accordance with an electromotive voltage group generated when the magnetic field emitted from a magnetic field generation element provided in a longitudinal direction of a probe is detected, a candidate vector calculation section that calculates a candidate vector based on the electromotive voltage group generated in the first magnetic field detection section and one piece of candidate position information, an estimated electromotive voltage calculation section that calculates an estimated electromotive voltage based on the one piece of candidate position information and the candidate vector and an estimated position acquiring section that acquires a candidate position that minimizes an error between the electromotive voltage group generated in the second magnetic field detection section and the estimated electromotive voltage as an estimated position of the magnetic field generation element.

9 Claims, 8 Drawing Sheets

(56) References Cited

FOREIGN PATENT DOCUMENTS

| JP | 09-084745 | 3/1997 |
| JP | 2000-081304 | 3/2000 |
| JP | 2002-340504 | 11/2002 |
| JP | 2003-114101 | 4/2003 |
| JP | 2006-149972 | 6/2006 |
| JP | 2006-247292 | 9/2006 |
| JP | 2009-047470 | 3/2009 |

* cited by examiner

PROBE SHAPE DETECTION APPARATUS AND PROBE SHAPE DETECTION METHOD

CROSS REFERENCE TO RELATED APPLICATION

This application is a continuation application of PCT/JP2011/062685 filed on Jun. 2, 2011 and claims benefit of Japanese Application No. 2010-132211 filed in Japan on Jun. 9, 2010, the entire contents of which are incorporated herein by this reference.

BACKGROUND OF THE INVENTION

1. Field of the Invention

The present invention relates to a probe shape detection apparatus and a probe shape detection method, and more particularly, to a probe shape detection apparatus and a probe shape detection method for detecting a shape of a probe using a magnetic field.

2. Description of the Related Art

When a probe such as an endoscope is inserted into a subject to perform an observation and treatment of a target region, it is possible to facilitate the insertion operation by concurrently using a detection apparatus capable of detecting the shape of the probe inserted in the subject. As such a detection apparatus, for example, one disclosed in Japanese Patent Application Laid-Open Publication No. 9-84745 is widely known.

Japanese Patent Application Laid-Open Publication No. 9-84745 discloses a technique that has a configuration in which a magnetic field detection element (sensing coil) can detect magnetic fields generated from a plurality of magnetic field generation elements (source coils) arranged in a probe and detects the shape of the probe based on an estimation result of estimating positions and orientations of the respective magnetic field generation elements so as to minimize a difference between a measured value of an actually produced voltage in the magnetic field detection element and an estimate value of a voltage estimated to be produced in the magnetic field detection element.

Furthermore, the aforementioned detection apparatus conventionally employs a technique of detecting the shape of a probe based on an estimation result of position information obtained through calculations using, for example, a Newton-Raphson method or multivariate analysis.

SUMMARY OF THE INVENTION

A probe shape detection apparatus according to the present invention includes a drive signal transmitting section that transmits a drive signal for causing a magnetic field to be generated from a magnetic field generation element provided along a longitudinal direction of a probe having an elongated shape, a first magnetic field detection section that detects the magnetic field emitted from the magnetic field generation element as magnetic field components in three mutually orthogonal axial directions and outputs a magnetic field detection signal corresponding to a first electromotive voltage group generated when detecting the magnetic field components in the three axial directions, a second magnetic field detection section provided at a position different from the first magnetic field detection section that detects the magnetic field emitted from the magnetic field generation element as magnetic field components in the three axial directions and outputs a magnetic field detection signal corresponding to a second electromotive voltage group generated when detecting the magnetic field components in the three axial directions, a candidate position storage section that stores a plurality of pieces of candidate position information indicating candidate positions that can be taken by the magnetic field generation element, a candidate vector calculation section that calculates candidate vectors indicating orientation of the magnetic field generation element when the magnetic field generation element is assumed to be located at a position corresponding to one piece of candidate position information based on the first electromotive voltage group and the one piece of candidate position information read from the candidate position storage section, an estimated electromotive voltage calculation section that calculates an estimated electromotive voltage estimated to be generated when the magnetic field emitted from the magnetic field generation element is detected based on the one piece of candidate position information read from the candidate position storage section and the candidate vector calculated in the candidate vector calculation section, an error calculation section that calculates an error between the second electromotive voltage group and the estimated electromotive voltage, an estimated position acquiring section that acquires a candidate position where the error is minimized among all candidate positions indicated as the candidate position information based on the calculation result of the error calculation section as an estimated position of the magnetic field generation element, and an image generation section that generates a shape detection image showing the shape of the probe based on the respective estimated positions acquired in the estimated position acquiring section.

A probe shape detection method according to the present invention includes a drive signal transmitting step of a drive signal transmitting section transmitting a drive signal for causing a magnetic field generated from a magnetic field generation element provided along a longitudinal direction of a probe having an elongated shape, a first magnetic field detecting step of a first magnetic field detection section detecting the magnetic field emitted from the magnetic field generation element as magnetic field components in three mutually orthogonal axial directions and outputting a magnetic field detection signal corresponding to a first electromotive voltage group generated when detecting the magnetic field components in the three axial directions, a second magnetic field detecting step of a second magnetic field detection section detecting the magnetic field emitted from the magnetic field generation element as magnetic field components in the three axial directions and outputting a magnetic field detection signal corresponding to a second electromotive voltage group generated when detecting the magnetic field components in the three axial directions, a candidate vector calculating step of a candidate vector calculation section calculating candidate vectors indicating orientation of the magnetic field generation element when the magnetic field generation element is assumed to be located at a position corresponding to the one piece of candidate position information based on the first electromotive voltage group and the one piece of candidate position information read from a candidate position storage section that stores a plurality of pieces of candidate position information indicating candidate positions that can be taken by the magnetic field generation element, an estimated electromotive voltage calculating step of an estimated electromotive voltage calculation section calculating an estimated electromotive voltage estimated to be generated when the magnetic field emitted from the magnetic field generation element is detected based on the one piece of candidate position information read from the candidate position storage section and the candidate vector calculated in the candidate vector calculating step, an error calculating step of an error calculation section calculating an error between the second electromotive voltage group and the estimated electromotive voltage, an estimated position acquiring step of an estimated position acquiring section acquiring a candidate position where the error is minimized among all candidate positions indicated as the candidate position information based on the calculation result of the error calculating step as an estimated position of the magnetic field generation element, and an image generating step of an image generation section generating a shape detection image showing a shape of the probe based on the respective estimated positions acquired in the estimated position acquiring step.

DETAILED DESCRIPTION OF THE PREFERRED EMBODIMENTS

Hereinafter, embodiments of the present invention will be described with reference to the drawings.

(First Embodiment)

FIG. 1 to FIG. 5 are related to a first embodiment of the present invention.

Figure 1:
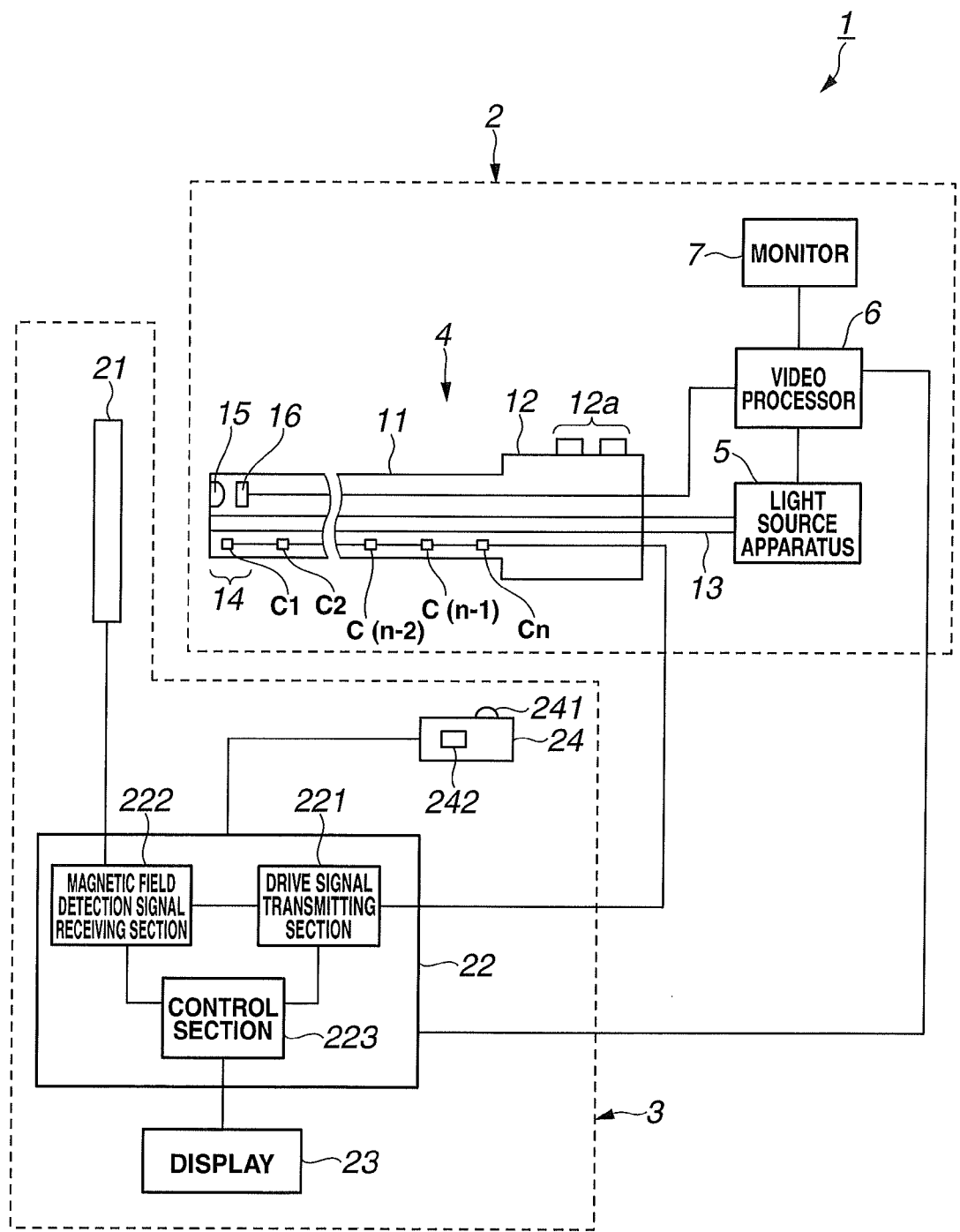
FIG. 1 is a diagram illustrating principal sections of a biological observation system including a probe shape detection apparatus according to an embodiment of the present invention.

A biological observation system 1 is configured by including an endoscope apparatus 2 that can observe an inside of a subject using an endoscope 4 and an endoscope shape detection apparatus 3 that can detect the shape of the endoscope 4 inserted in the subject as shown in FIG. 1.

The endoscope apparatus 2 is configured by including the endoscope 4 that picks up an image of an object in the subject and outputs an image pickup signal, a light source apparatus 5 that supplies illuminating light for illuminating the object (e.g., frame sequential RGB light) to the endoscope 4, a video processor 6 that applies signal processing to the image pickup signal outputted from the endoscope 4 and outputs a video signal, and a monitor 7 that displays an image of the object according to the video signal outputted from the video processor 6.

The endoscope 4 that functions as a probe is configured by including an insertion portion 11 which is flexible and has an elongated shape and an operation section 12 provided at a rear end of the insertion portion 11.

A light guide 13 configured as a light conduction path that transmits the illuminating light supplied from the light source apparatus 5 to an illuminating window (not shown) provided in a distal end portion 14 of the insertion portion 11 is inserted and arranged along a longitudinal direction inside the insertion portion 11. That is, the illuminating light supplied from the light source apparatus 5 is emitted onto the object via at least the light guide 13 and the illuminating window.

Furthermore, a plurality of source coils C1, C2, ..., Cn (abbreviated as C1 to Cn) which are magnetic field generation elements are arranged along a longitudinal direction at predetermined intervals inside the insertion portion 11. A description will be given in the present embodiment assuming that the source coil C1 is arranged closest to the distal end of the insertion portion 11 and the source coil Cn is arranged closest to the proximal end of the insertion portion 11.

The source coils C1 to Cn emit magnetic fields around corresponding to a drive signal outputted from the endoscope shape detection apparatus 3. The magnetic fields emitted from the source coils C1 to Cn are detected by a sensing coil unit 21 of the endoscope shape detection apparatus 3.

A bending portion (not shown) is provided on a rear end side of the distal end portion 14 of the insertion portion 11. The bending portion can be bent in a desired direction according to the operation of e.g., a bending operation knob (not shown) provided in the operation section 12. The operation section 12 of the endoscope 4 is provided with a scope switch group 12a with which operation instruction can be given associated with e.g., switching between ON and OFF of various functions realized by the biological observation system 1 in addition to the aforementioned bending operation knob.

On the other hand, an observation window (not shown) furnished with an objective lens 15 is provided at a position adjacent to the illuminating window (not shown) in the distal end portion 14. Furthermore, an image pickup surface of an image pickup device 16 made up of a CCD or the like is arranged at an image forming position of the objective lens 15.

The image pickup device 16 is electrically connected to the video processor 6 via a signal line, generates an image pickup signal according to an optical image of the object formed by the objective lens 15 and outputs the image pickup signal to the video processor 6.

When supplying, for example, frame sequential RGB light as illuminating light, the light source apparatus 5 outputs a synchronization signal which is synchronized with a period of time during which each light is supplied to the video processor 6. In this case, suppose the video processor 6 performs signal processing in synchronization with the synchronization signal outputted from the light source apparatus 5.

The endoscope shape detection apparatus 3 that functions as a probe shape detection apparatus is configured by including the sensing coil unit 21 that outputs a magnetic field detection signal according to detection results of magnetic fields emitted from the source coils C1 to Cn, an endoscope shape calculation processing apparatus 22 that estimates the shape (insertion shape) of the insertion portion 11 based on the magnetic field detection signal outputted from the sensing coil unit 21, a display 23 that displays an image (shape detection image) according to a processing result of the endoscope shape calculation processing apparatus 22, a reference position specification apparatus 24 that specifies a reference position of the image (shape detection image) displayed on the display 23.

The sensing coil unit 21 is configured to be able to be disposed, for example, in a periphery of an inspection bed on which a patient lies on his/her side and able to output a magnetic field detection signal according to detection results of magnetic fields emitted from the source coils C1 to Cn to the endoscope shape calculation processing apparatus 22.

Figure 2:
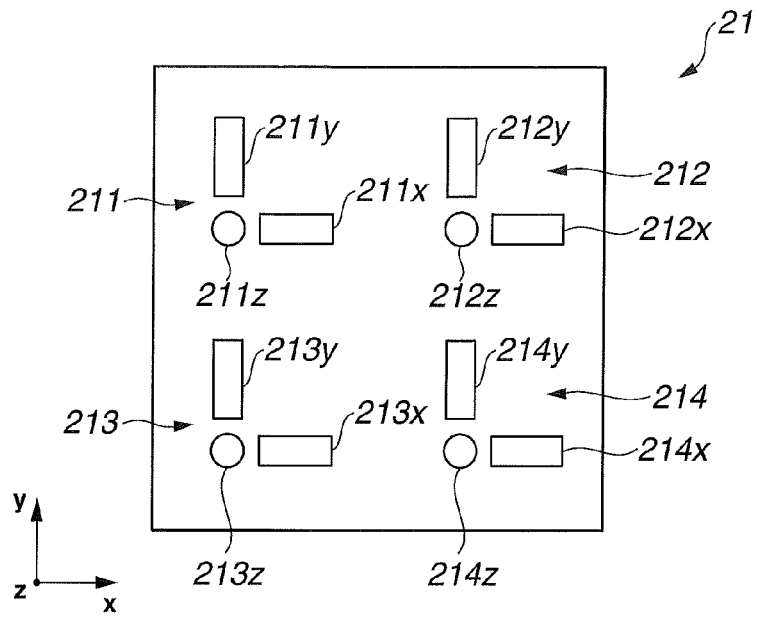
FIG. 2 is a diagram illustrating an example of a layout of coil groups provided in a sensing coil unit viewed from the front of the sensing coil unit.

Furthermore, as shown in FIG. 2, the sensing coil unit 21 includes coil groups 211, 212, 213 and 214 configured to be able to detect magnetic fields emitted from the source coils C1 to Cn as magnetic field components in three mutually orthogonal axial directions.

The coil group 211 is configured as a combination of three coils; a coil 211$x$ disposed toward the x-axis direction corresponding to the left/right direction of the sensing coil unit 21, a coil 211$y$ disposed toward the y-axis direction corresponding to the upward/downward direction of the sensing coil unit 21, and a coil 211$z$ disposed toward the z-axis direction corresponding to the depth direction of the sensing coil unit 21.

The coil group 212 is configured as a combination of three coils; a coil 212$x$ disposed toward the x-axis direction corresponding to the left/right direction of the sensing coil unit 21, a coil 212$y$ disposed toward the y-axis direction corresponding to the upward/downward direction of the sensing coil unit 21, and a coil 212$z$ disposed toward the z-axis direction corresponding to the depth direction of the sensing coil unit 21.

The coil group 213 is configured as a combination of three coils; a coil 213$x$ disposed toward the x-axis direction corresponding to the left/right direction of the sensing coil unit 21, a coil 213$y$ disposed toward the y-axis direction corresponding to the upward/downward direction of the sensing coil unit 21, and a coil 213$z$ disposed toward the z-axis direction corresponding to the depth direction of the sensing coil unit 21.

The coil group 214 is configured as a combination of three coils; a coil 214$x$ disposed toward the x-axis direction corresponding to the left/right direction of the sensing coil unit 21, a coil 214$y$ disposed toward the y-axis direction corresponding to the upward/downward direction of the sensing coil unit 21, and a coil 214$z$ disposed toward the z-axis direction corresponding to the depth direction of the sensing coil unit 21.

According to the above-described configuration, when, for example, a magnetic field is emitted from a source coil Cp ($1 \le p \le n$), electromotive voltages corresponding to the magnetic field components in the x-axis direction of the magnetic field are generated in the coils 211$x$ to 214$x$, and then magnetic field detection signals corresponding to the electromotive voltages are outputted to the endoscope shape calculation processing apparatus 22. Furthermore, according to the above-described configuration, when, for example, a magnetic field is emitted from the source coil Cp, electromotive voltages corresponding to the magnetic field components in the y-axis direction of the magnetic field are generated in the coils 211$y$ to 214$y$, and then magnetic field detection signals corresponding to the electromotive voltages are outputted to the endoscope shape calculation processing apparatus 22. Furthermore, according to the above-described configuration, when, for example, a magnetic field is emitted from the source coil Cp, electromotive voltages corresponding to magnetic field components in the z-axis direction of the magnetic field are generated in the coils 211$z$ to 214$z$, and then magnetic field detection signals corresponding to the electromotive voltages are outputted to the endoscope shape calculation processing apparatus 22.

As shown in FIG. 1, the endoscope shape calculation processing apparatus 22 is configured by including a drive signal transmitting section 221, a magnetic field detection signal receiving section 222, and a control section 223. Furthermore, the endoscope shape calculation processing apparatus 22 is configured to be able to communicate with the video processor 6 via a signal line.

The drive signal transmitting section 221 transmits, to the endoscope 4, drive signals to simultaneously drive a plurality of coils of the source coils C1 to Cn at different frequencies. Alternatively, the drive signal transmitting section 221 transmits, to the endoscope 4, drive signals to sequentially drive the source coils C1 to Cn at the same frequency one by one. The latter case will be described in the present embodiment, that is, a case where drive signals to sequentially drive the source coils C1 to Cn at the same frequency are transmitted to the endoscope 4 one by one. When such drive signals are transmitted, an AC magnetic field is thereby generated for each source coil at individual timing The magnetic field detection signal receiving section 222 applies signal processing such as frequency separation to each magnetic field detection signal outputted from the sensing coil unit 21. The magnetic field detection signal receiving section 222 then divides each magnetic field detection signal after the signal processing by coil group and outputs the resulting signals.

Figure 3:
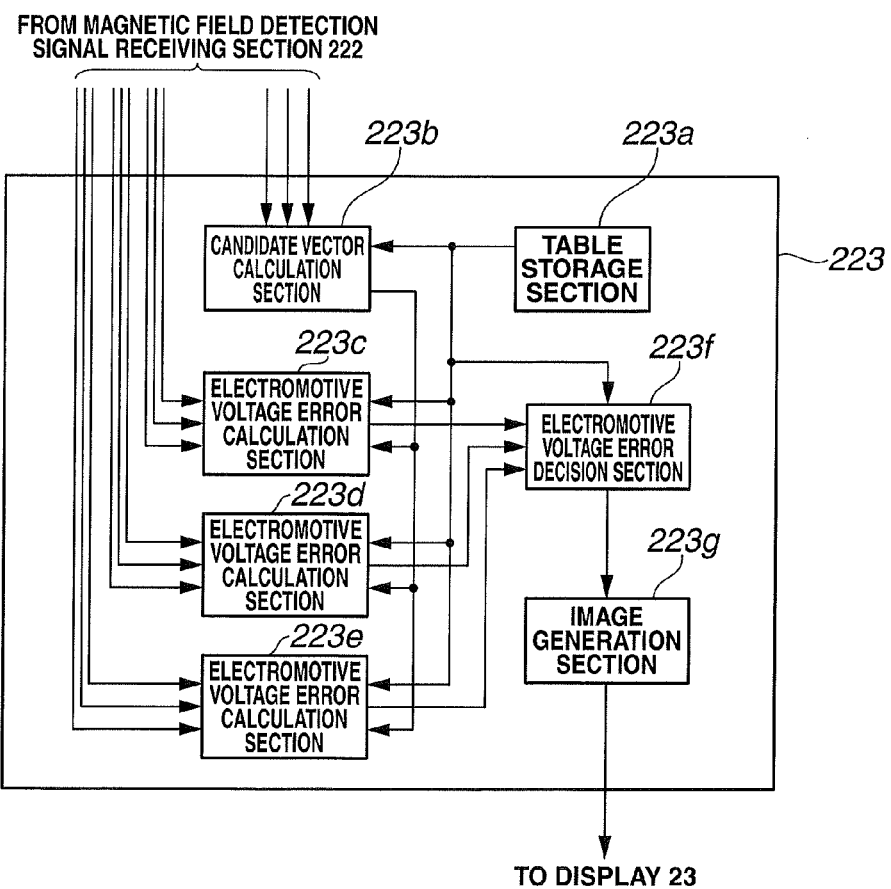
FIG. 3 is a block diagram illustrating an example of a specific configuration of a control section provided in an endoscope shape calculation processing apparatus according to a first embodiment.

As shown in FIG. 3, the control section 223 is configured by including a table storage section 223$a$, a candidate vector calculation section 223$b$, electromotive voltage error calculation sections 223$c$, 223$d$ and 223$e$, an electromotive voltage error decision section 223$f$, and an image generation section 223$g$. Furthermore, the control section 223 is configured to be able to perform control on the drive signal transmitting section 221 associated with the outputs of drive signals to the source coils C1 to Cn. Through such control of the control section 223, the drive signal transmitting section 221, for example, outputs drive signals so as to drive the source coils C1 to Cn one by one.

Figure 4:
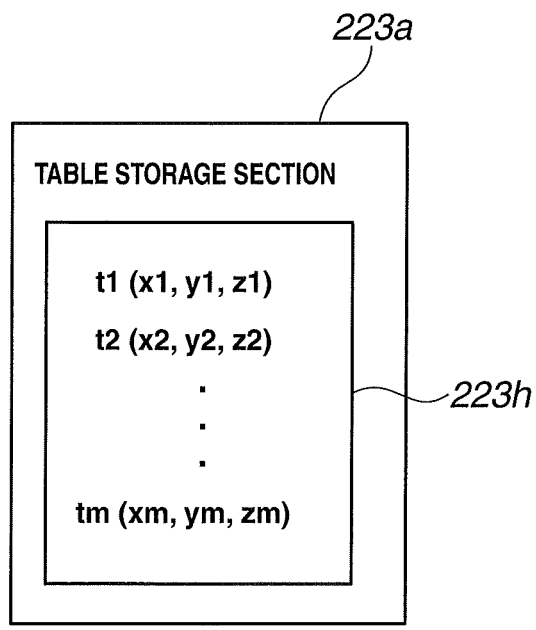
FIG. 4 is a diagram illustrating table data stored in a table storage section.

The table storage section 223$a$ stores m pieces of coordinate data corresponding to candidate positions that can be taken by the source coils C1 to Cn within a magnetic field detection range of the sensing coil unit 21 as table data. To be more specific, the table storage section 223$a$ stores, for example, table data 223$h$ including m pieces of coordinate data t1 (x1, y1, z1) to tm (xm, ym, zm) as shown in FIG. 4.

The candidate vector calculation section 223$b$ reads coordinate data tq ($1 \le q \le m$) from the coordinate data included in the table data 223$h$ of the table storage section 223$a$. After that, the candidate vector calculation section 223$b$ calculates a candidate vector corresponding to the coordinate data tq based on the coordinate data tq read from the table storage section 223$a$ and voltages (signal levels) of the magnetic field detection signals outputted from the three coils (211$x$, 211$y$ and 211$z$) of the coil group 211 via the magnetic field detection signal receiving section 222, and outputs the calculation results to the electromotive voltage error calculation section 223$c$, 223$d$ and 223$e$ respectively.

The aforementioned candidate vector is a parameter indicating the orientation of the source coil when the source coil is assumed to exist at a position corresponding to the coordinate data tq.

The electromotive voltage error calculation section 223c reads the same coordinate data tq read by the candidate vector calculation section 223b from each piece of coordinate data included in the table data 223h of the table storage section 223a. After that, the electromotive voltage error calculation section 223c calculates an estimated electromotive voltage corresponding to the coordinate data tq based on the coordinate data tq read from the table storage section 223a and the calculation result of the candidate vector outputted from the candidate vector calculation section 223b. The electromotive voltage error calculation section 223c calculates electromotive voltage errors $\Delta vx1$, $\Delta vy1$ and $\Delta vz1$ which are differences between the voltages (signal levels) of the magnetic field detection signals outputted from the three coils (212x, 212y and 212z) of the coil group 212 via the magnetic field detection signal receiving section 222 and the aforementioned estimated electromotive voltage and outputs the calculation results to the electromotive voltage error decision section 223f.

When it is assumed that the source coil exists at a position corresponding to the coordinate data tq and the source coil is oriented toward the candidate vector outputted from the candidate vector calculation section 223b, the aforementioned estimated electromotive voltage is a parameter indicating the value of an electromotive voltage estimated to be generated when the magnetic field emitted from the source coil is detected.

The electromotive voltage error calculation section 223d reads the same coordinate data tq read by the candidate vector calculation section 223b from the respective coordinate data included in the table data 223h of the table storage section 223a. After that, the electromotive voltage error calculation section 223d calculates an estimated electromotive voltage corresponding to the coordinate data tq based on the coordinate data tq read from the table storage section 223a and the calculation result of the candidate vector outputted from the candidate vector calculation section 223b. The electromotive voltage error calculation section 223d then calculates electromotive voltage errors $\Delta vx2$, $\Delta vy2$ and $\Delta vz2$ which are differences between voltages (signal levels) of the magnetic field detection signals outputted from the three coils (213x, 213y and 213z) of the coil group 213 via the magnetic field detection signal receiving section 222 and the aforementioned estimated electromotive voltage, and outputs the calculation results to the electromotive voltage error decision section 223f.

The electromotive voltage error calculation section 223e reads the same coordinate data tq read by the candidate vector calculation section 223b from the coordinate data included in the table data 223h of the table storage section 223a. After that, the electromotive voltage error calculation section 223e calculates an estimated electromotive voltage corresponding to the coordinate data tq based on the coordinate data tq read from the table storage section 223a and the calculation result of the candidate vector outputted from the candidate vector calculation section 223b. The electromotive voltage error calculation section 223e then calculates electromotive voltage errors $\Delta vx3$, $\Delta vy3$ and $\Delta vz3$ which are differences between voltages (signal levels) of the magnetic field detection signals outputted from the three coils (214x, 214y and 214z) of the coil group 214 via the magnetic field detection signal receiving section 222 and the aforementioned estimated electromotive voltage and outputs the calculation results to the electromotive voltage error decision section 223f.

The electromotive voltage error decision section 223f performs decision processing based on the result of adding electromotive voltage error values ($\Delta vx1$, $\Delta vy1$, $\Delta vz1$, $\Delta vx2$, $\Delta vy2$, $\Delta vz2$, $\Delta vx3$, $\Delta vy3$ and $\Delta vz3$) outputted from the electromotive voltage error calculation sections 223c, 223d and 223e respectively, thereby acquires estimated positions of the respective source coils from the respective coordinate data included in the table data 223h and sequentially stores the estimated positions. Upon completing the storage of the estimated positions of the source coils C1 to Cn, the electromotive voltage error decision section 223f outputs the estimated positions to the image generation section 223g. Details of the aforementioned decision processing will be described later.

The image generation section 223g generates a shape detection image showing the shape of the insertion portion 11 based on the estimated positions of the source coils C1 to Cn outputted from the electromotive voltage error decision section 223f. Furthermore, the image generation section 223g sets the display position, for example, so that the side of the shape detection image closest to the root (proximal end side) is displayed at the center of the bottom of the display screen of the display 23 based on a reference position specified by the reference position specification apparatus 24. The image generation section 223g then generates a video signal based on the shape detection image set at the display position and outputs the video signal to the display 23.

The reference position specification apparatus 24 is connected to the endoscope shape calculation processing apparatus 22, and has a switch 241 and a coil 242 operated by an operator or the like.

The switch 241 is configured to be able to instruct the drive signal transmitting section 221 to turn ON/OFF the state of generation of a magnetic field from the coil 242 according to the operation by the operator or the like. According to such a configuration, when the switch 241 gives an instruction for generating a magnetic field (turning ON the state of generation of a magnetic field) from the coil 242, a drive signal from the drive signal transmitting section 221 that has received the instruction is supplied to the coil 242, and a magnetic field corresponding to the drive signal is emitted from the coil 242.

The magnetic field emitted from the coil 242 is outputted from the sensing coil unit 21 as a magnetic field detection signal corresponding to the detection result of the magnetic field, passed through the magnetic field detection signal receiving section 222 and then inputted to the control section 223. After that, processing based on the magnetic field detection signal is performed at the respective sections of the table storage section 223a, the candidate vector calculation section 223b, the electromotive voltage error calculation section 223c, the electromotive voltage error calculation section 223d, the electromotive voltage error calculation section 223e and the electromotive voltage error decision section 223f of the control section 223, and an estimated position of the coil 242 can be obtained. The image generation section 223g sets the display position of the shape detection image using the estimated position of the coil 242 as the aforementioned reference position.

Next, the operation of the present embodiment will be described.

First, the operator or the like connects the respective sections of the biological observation system 1 and then supplies power to the respective sections as shown in FIG. 1.

Immediately after power is supplied thereto, the endoscope shape calculation processing apparatus 22 performs a selfdiagnosis associated with the presence or absence of fault locations. To be more specific, immediately after power is supplied thereto, the respective sections of the endoscope shape calculation processing apparatus 22 transmit/receive a fault diagnosis signal through three paths of the drive signal transmitting section 221 the magnetic field detection signal receiving section 222, the magnetic field detection signal receiving section 222 the control section 223, and the control section 223 the drive signal transmitting section 221. Upon detecting that the fault diagnosis signal has not been transmitted/received in at least one of the aforementioned three paths, the endoscope shape calculation processing apparatus 22 notifies the operator or the like of the fact that a fault location exists in itself by performing an operation such as blinking of an LED (not shown) provided on the outer surface of itself.

On the other hand, after confirming that there is no fault location in the endoscope shape calculation processing apparatus 22, the operator or the like places the reference position specification apparatus 24 in the vicinity of the anus of a patient lying on the inspection bed (not shown), operates the switch 241 and thereby gives an instruction for generating a magnetic field from the coil 242 (turning ON the state of generation of the magnetic field).

The magnetic field emitted from the coil 242 is outputted as a magnetic field detection signal according to the detection result of the magnetic field in the sensing coil unit 21, passed through the magnetic field detection signal receiving section 222 and then inputted to the control section 223. After that, the magnetic field detection signal is subjected to processing based on the magnetic field detection signal in the respective sections of the table storage section 223a, the candidate vector calculation section 223b, the electromotive voltage error calculation section 223c, the electromotive voltage error calculation section 223d, the electromotive voltage error calculation section 223e and the electromotive voltage error decision section 223f of the control section 223, and an estimated position of the coil 242 is thereby acquired. The image generation section 223g then sets the display position of the shape detection image using the estimated position of the coil 242 as the aforementioned reference position.

In the above-described case, the reference position is specified so that the position corresponding to the vicinity of the anus of the patient is located at the center of the bottom in the display screen of the display 23. That is, when performing an observation using the type of endoscope 4 inserted from the anus of the patient, the display position is set so that the side of the shape detection image closest to the root (proximal end side) is displayed at the center of the bottom in the display screen of the display 23 by specifying the position corresponding to the anus of the patient as the reference position.

According to the present embodiment, it may also be possible to realize an operation associated with specification of a reference position by providing one of the switches of the scope switch group 12a with the function of the switch 241 and providing the source coil Cn located closest to the proximal end side of the insertion portion 11 with the function of the coil 242. In such a case, the operator or the like may generate a magnetic field from the source coil Cn by inserting the insertion portion 11 up to the position at which the source coil Cn is disposed and then operating the scope switch group 12a.

Furthermore, according to the present embodiment, only the coil 242 may be provided in the reference position specification apparatus 24 and a predetermined key of a keyboard (not shown) connectable to the video processor 6 or the endoscope shape calculation processing apparatus 22 may be provided with the function of the switch 241.

The operator or the like performs an operation associated with the specification of the reference position using the reference position specification apparatus 24, and then inserts the insertion portion 11 into the body cavity of the patient while watching the image of the object displayed on the monitor 7. Furthermore, almost simultaneously with the starting of the insertion of the insertion portion 11 into the body cavity of the patient, magnetic fields are emitted from the source coils C1 to Cn.

Here, the operation and processing or the like of the endoscope shape detection apparatus 3 of the present embodiment will be described with reference to the flowchart in FIG. 5. For simplicity of description, a case will be described as an example where magnetic fields emitted from the respective source coils are detected in the order of the source coils C1, C2, ..., Cn and magnetic field detection signals are outputted in that order.

Figure 5:
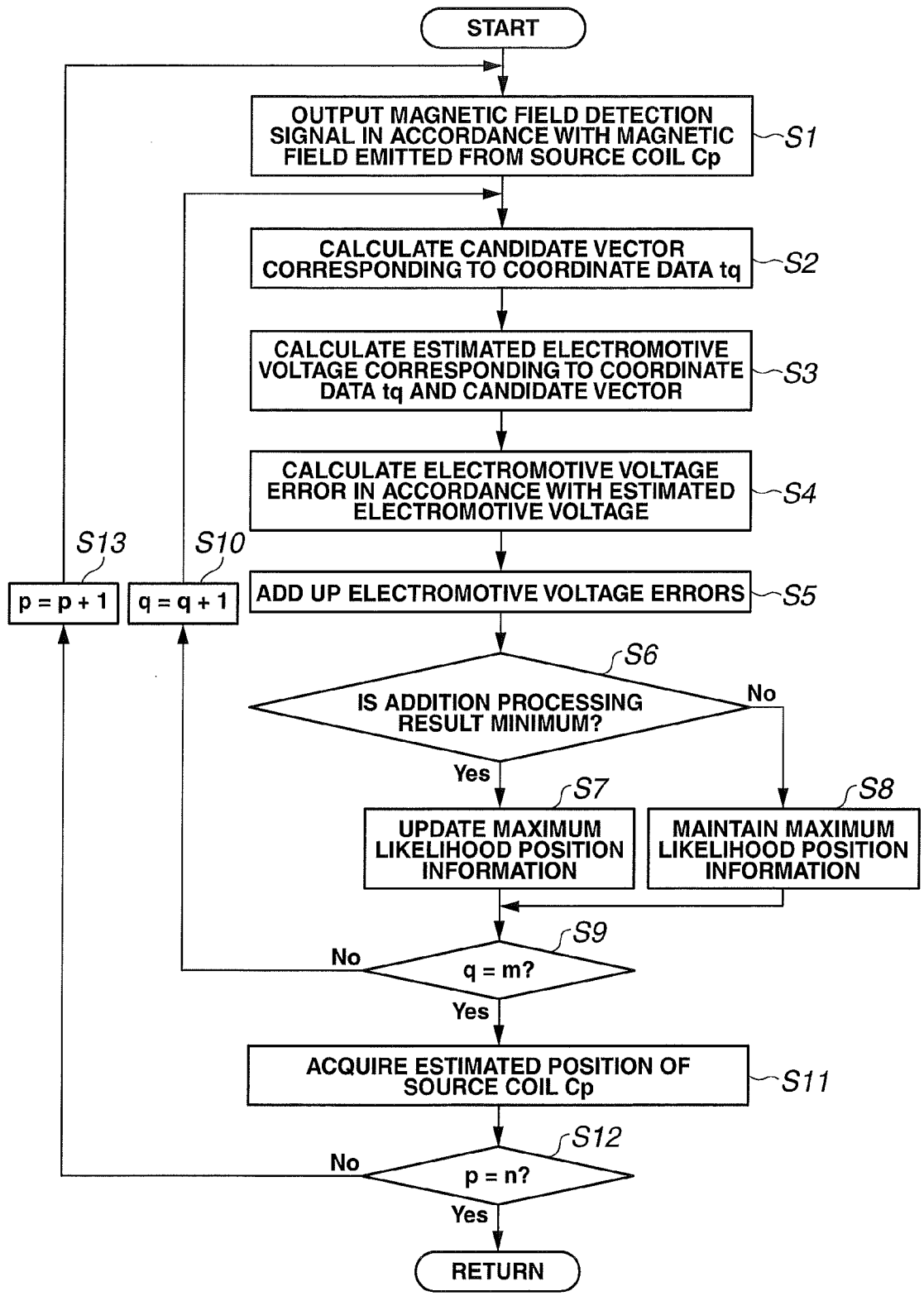
FIG. 5 is a flowchart illustrating processing and operation or the like carried out by the probe shape detection apparatus of the first embodiment.

When a magnetic field is emitted from the source coil Cp, a magnetic field detection signal in accordance with the magnetic field is outputted from each coil of the coil groups 211, 212, 213 and 214 (step S1 in FIG. 5).

The candidate vector calculation section 223b reads the coordinate data tq from the coordinate data included in the table data 223h of the table storage section 223a. Then, the candidate vector calculation section 223b calculates a candidate vector corresponding to the coordinate data tq (step S2 in FIG. 5) based on the coordinate data tq read from the table storage section 223a and voltages (signal levels) of the magnetic field detection signals outputted from the three coils (211x, 211y and 211z) of the coil group 211 via the magnetic field detection signal receiving section 222 and outputs the calculation results to the electromotive voltage error calculation sections 223c, 223d and 223e respectively.

The electromotive voltage error calculation sections 223c, 223d and 223e read the same coordinate data tq read by the candidate vector calculation section 223b from the respective coordinate data included in the table data 223h of the table storage section 223a. After that, the electromotive voltage error calculation sections 223c, 223d and 223e calculate estimated electromotive voltages corresponding to the coordinate data tq based on the coordinate data tq read from the table storage section 223a and the calculation result of a candidate vector outputted from the candidate vector calculation section 223b (step S3 in FIG. 5).

The electromotive voltage error calculation section 223c calculates electromotive voltage errors $\Delta vx1$, $\Delta vy1$ and $\Delta vz1$ which are differences between voltages (signal levels) of the magnetic field detection signals outputted from the three coils (212x, 212y and 212z) of the coil group 212 via the magnetic field detection signal receiving section 222 and the aforementioned estimated electromotive voltage and outputs the calculation results to the electromotive voltage error decision section 223f (step S4 in FIG. 5).

The electromotive voltage error calculation section 223d calculates electromotive voltage errors $\Delta vx2$, $\Delta vy2$ and $\Delta vz2$ which are differences between voltages (signal levels) of the magnetic field detection signals outputted from the three coils (213x, 213y and 213z) of the coil group 213 via the magnetic field detection signal receiving section 222 and the aforementioned estimated electromotive voltage and outputs the calculation results to the electromotive voltage error decision section 223f (step S4 in FIG. 5).

The electromotive voltage error calculation section 223e calculates electromotive voltage errors $\Delta vx3$, $\Delta vy3$ and $\Delta vz3$ which are differences between voltages (signal levels) of the magnetic field detection signals outputted from the three coils (214$x$, 214$y$ and 214$z$) of the coil group 214 via the magnetic field detection signal receiving section 222 and the aforementioned estimated electromotive voltage and outputs the calculation results to the electromotive voltage error decision section 223$f$ (step S4 in FIG. 5).

The electromotive voltage error decision section 223$f$ adds up the values of the electromotive voltage errors outputted respectively from the electromotive voltage error calculation sections 223$c$, 223$d$ and 223$e$ ($\Delta$vx1, $\Delta$vy1, $\Delta$vz1, $\Delta$vx2, $\Delta$vy2, $\Delta$vz2, $\Delta$vx3, $\Delta$vy3 and $\Delta$vz3) (step S5 in FIG. 5). Furthermore, almost simultaneously with such addition processing of electromotive voltage errors, the electromotive voltage error decision section 223$f$ reads the same coordinate data tq read by the candidate vector calculation section 223$b$.

After that, the electromotive voltage error decision section 223$f$ decides whether or not the addition processing result of the electromotive voltage errors corresponding to the coordinate data tq is a minimum with respect to the addition processing result of electromotive voltage errors obtained earlier (step S6 in FIG. 5). Upon deciding the addition processing result of the electromotive voltage errors corresponding to the coordinate data tq is a minimum, the electromotive voltage error decision section 223$f$ then updates a maximum likelihood position information in accordance with the addition processing result (step S7 in FIG. 5) and moves to the processing in step S9 in FIG. 5. Furthermore, upon deciding that the addition processing result of the electromotive voltage errors corresponding to the coordinate data tq is not a minimum, the electromotive voltage error decision section 223$f$ discards the addition processing result and moves to the processing in step S9 in FIG. 5 while maintaining the maximum likelihood position information obtained earlier (step S8 in FIG. 5).

The aforementioned maximum likelihood position information is information stored in a memory (not shown) provided for the electromotive voltage error decision section 223$f$ and contains the addition processing result when the addition processing result of the electromotive voltage errors becomes a minimum value and one piece of coordinate data associated with the addition processing result. That is, the decision processing in step S6 in FIG. 5 is performed by comparing the addition processing result obtained by reading maximum likelihood position information stored in the memory of the electromotive voltage error decision section 223$f$ with the addition processing result of the electromotive voltage errors obtained in step S5 in FIG. 5.

In accordance with the processing result of such decision processing, the maximum likelihood position information stored in the memory of the electromotive voltage error decision section 223$f$ is rewritten as appropriate. However, when q=1, since there is no earlier maximum likelihood position information, the process moves to step S7 without performing the decision processing in step S6 in FIG. 5, and the addition processing result of electromotive voltage errors obtained in step S5 and the coordinate data t1 associated with the addition processing result are stored in the memory of the electromotive voltage error decision section 223$f$ as maximum likelihood position information.

On the other hand, when processing on all coordinate data t1 to tm in the respective sections of the above-described control section 223 is not completed (step S9 in FIG. 5), after the next coordinate data t(q+1) is read (step S10 in FIG. 5), the processes in step S2 to step S8 in FIG. 5 are performed using the coordinate data t(q+1). Furthermore, when the processing on all coordinate data t1 to tm is completed (step S9 in FIG. 5), the electromotive voltage error decision section 223$f$ acquires coordinate data included in the maximum likelihood position information stored in itself at that point as an estimated position of the source coil Cp (step S11 in FIG. 5).

When the estimated positions of all the source coils C1 to Cn are not obtained (step S12 in FIG. 5), the processes in step 51 to step S11 in FIG. 5 are performed based on the magnetic field detection signal according to the magnetic field emitted from the next source coil C(p+1) (step S13 in FIG. 5). Furthermore, when the estimated positions of all the source coils C1 to Cn are obtained, the electromotive voltage error decision section 223$f$ outputs the information on the estimated positions of the source coils C1 to Cn to the image generation section 223$g$.

The image generation section 223$g$ generates a shape detection image showing the shape of the insertion portion 11 based on the estimated positions of the source coils C1 to Cn outputted from the electromotive voltage error decision section 223$f$. Furthermore, the image generation section 223$g$ sets the display position so that the side of the shape detection image closest to the root (proximal end side) is displayed at the center of the bottom in the display screen of the display 23 based on the reference position specified by the reference position specification apparatus 24. The image generation section 223$g$ generates a video signal based on the shape detection image whose display position is set and outputs the video signal to the display 23.

As described so far, according to the present embodiment, it is possible to obtain the estimated position of a source coil without the need for calculation using the orientation of the source coil as a variable. For this reason, according to the present embodiment, it is possible to reduce the amount of calculation when obtaining the estimated position of a source coil, that is, shorten the time required to detect the shape of the probe inserted in the subject compared to the conventional art.

Furthermore, according to the present embodiment, as the amount of calculation when obtaining the estimated position of the source coil decreases, it is possible to improve a frame rate, that is, more smoothly display the shape detection image showing the shape of the probe inserted in the subject compared to the conventional art. (According to the present embodiment, the frame rate can be improved up to on the order of approximately three times the conventional one.)

Furthermore, according to the present embodiment, as the amount of calculation when obtaining the estimated position of the source coil decreases, it is possible to improve the responsivity with respect to the insertion operation (and removing operation) of the insertion portion and consequently support the insertion operation (and removing operation) of the insertion portion.

According to the conventional calculation using a Newton-Raphson method or multivariate analysis, when, for example, the distance between the source coil and the sensing coil unit is short, divergence of solutions occurs, that is, there can be a situation in which estimated positions of the source coils cannot be obtained. Furthermore, according to the conventional calculation using the Newton-Raphson method or multivariate analysis, there can also be a situation in which the calculation time required to obtain estimated positions of the source coils according to the distance between the source coils and the sensing coil unit becomes unstable. In contrast, the present embodiment is configured such that the calculation count when obtaining the estimated position of one source coil is limited to a certain count and a unique estimated position of one source coil may be obtained through the certain count of calculation. As a result, the present embodiment can improve the image quality of a shape detection image showing the shape of the probe inserted in the subject compared to the conventional art.

The sensing coil unit 21 of the present embodiment is not necessarily configured by including the four coil groups 211 to 214 as long as it has at least one candidate vector calculation coil group made up of coils arranged along the x-axis direction, y-axis direction and z-axis direction respectively and one electromotive voltage error calculation coil group made up of coils arranged along the x-axis direction, y-axis direction and z-axis direction respectively.

Furthermore, the present embodiment is not limited to the configuration in which estimated positions of all source coils C1 to Cn are acquired and shape detection images are generated, but may also have a configuration in which, for example, estimated positions of a predetermined one source coil (e.g., source coil C1) are time-sequentially acquired and transformed into graphics to thereby generate detection images corresponding to tracks of the movement of the predetermined one source coil.

Furthermore, the present embodiment is not limited to the configuration in which in the processing shown in step S2 to step S10 in FIG. 5, the processing on all coordinate data included in the table data 223h is repeated to acquire estimated positions of the source coil every time, but may also have a configuration in which, for example, of all coordinate data included in the table data 223h, only coordinate data within a predetermined range with reference to the last acquired estimated position of the source coil Cp or coordinate data within a range calculated using the last acquired estimated position of the source coil Cp may be read and subjected to processing to thereby acquire the estimated position of the source coil Cp this time. To be more specific, for example, of the respective coordinate data included in the table data 223h, a coordinate data group located within a range in which the distance from the coordinate data corresponding to the last acquired estimated position of the source coil Cp falls to or below a predetermined value may be exclusively read to thereby reduce (narrow) the number of pieces of coordinate data used for processing when acquiring the estimated position of the source coil Cp this time.

(Second Embodiment)

Figure 6:
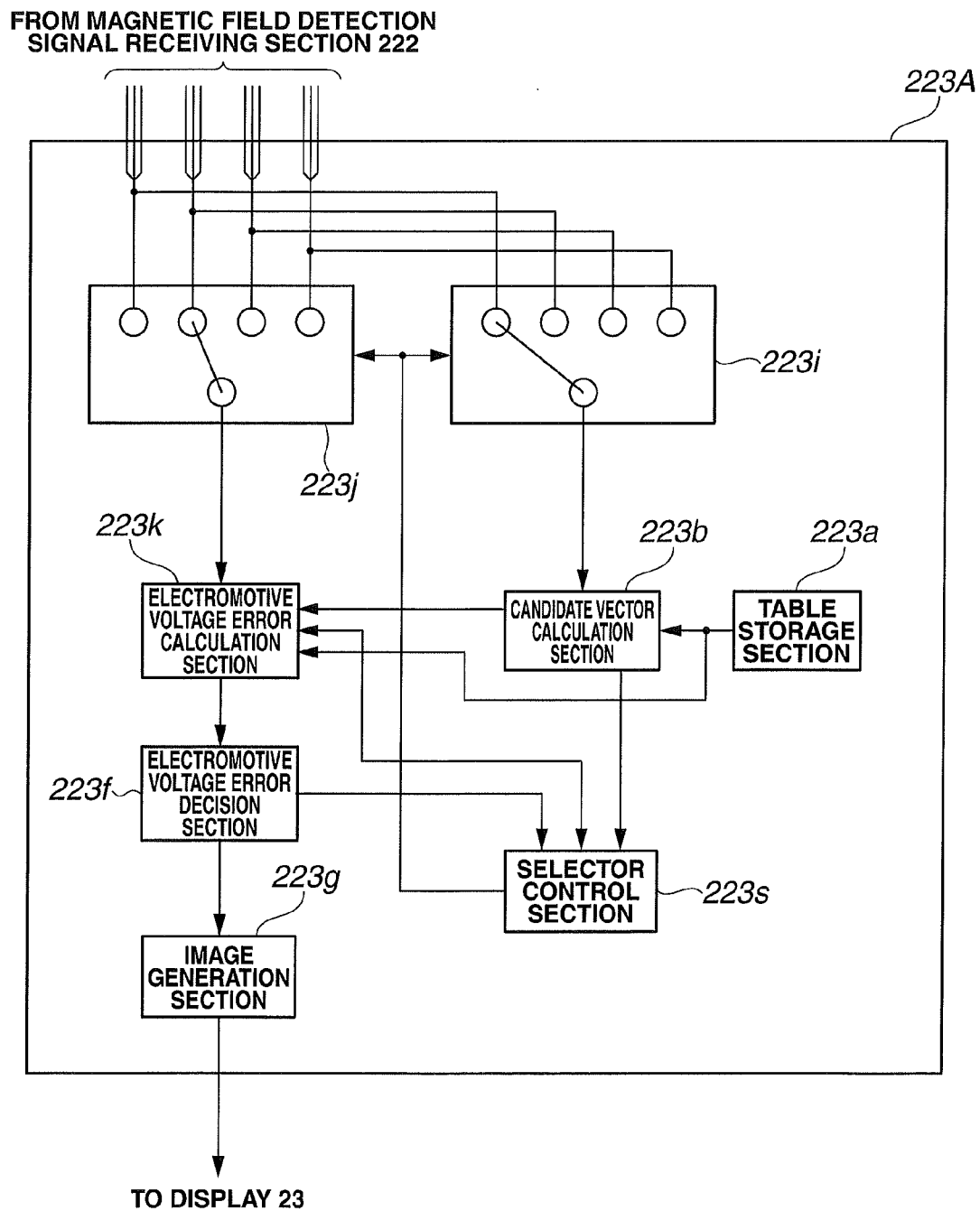
FIG. 6 is a block diagram illustrating an example of a specific configuration of the control section provided in the endoscope shape calculation processing apparatus according to a second embodiment.
Figure 7:
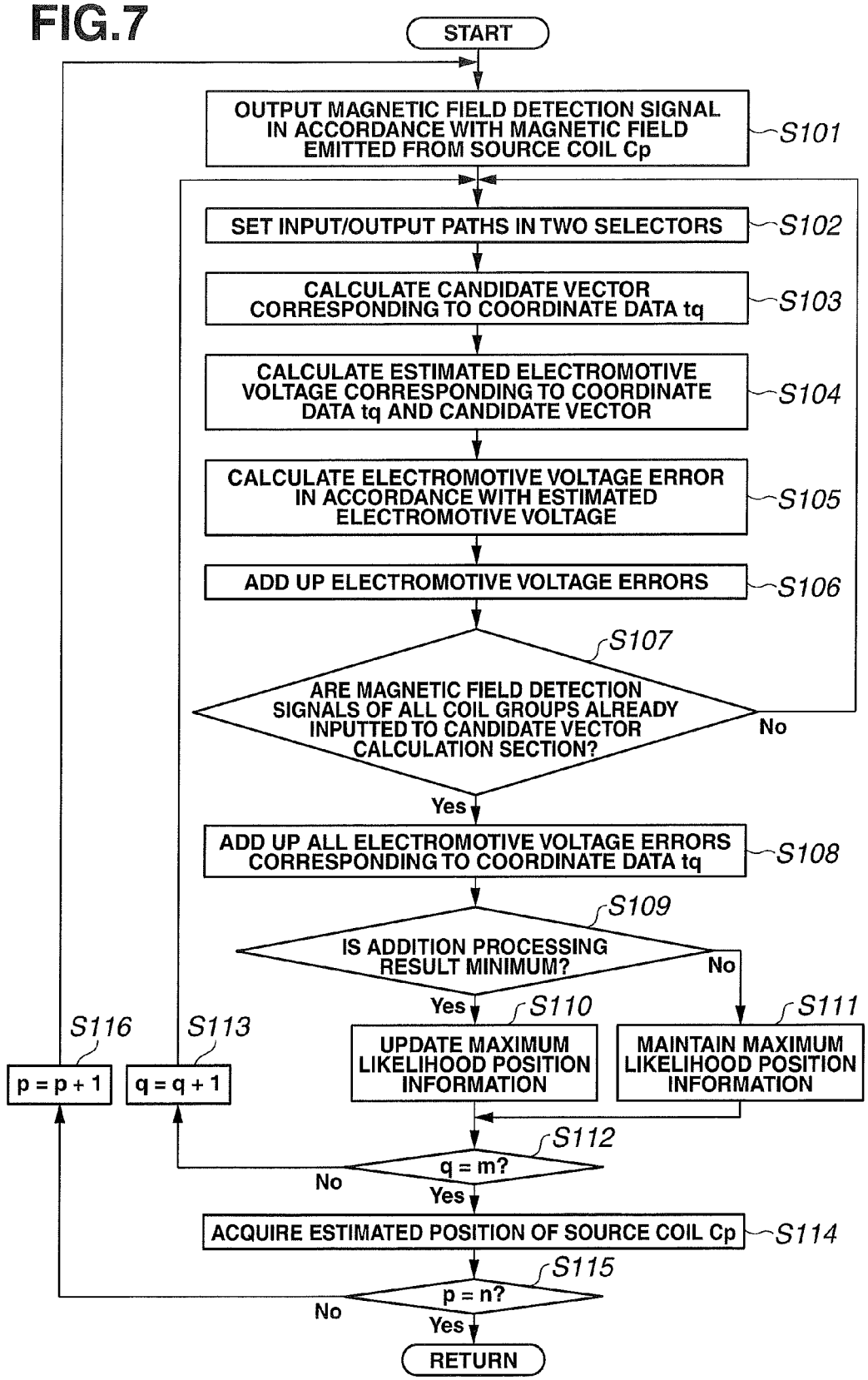
FIG. 7 is a flowchart illustrating processing and operation or the like in the probe shape detection apparatus according to the second embodiment.

FIG. 6 and FIG. 7 are related to a second embodiment of the present invention.

Detailed descriptions of parts in the present embodiment having configurations or the like identical to those of the first embodiment will be omitted and the parts having configurations or the like different from those in first embodiment will be mainly described.

A biological observation system according to the present embodiment is configured by including a control section 223A instead of the control section 223 according to the first embodiment and the rest of the configuration is similar to the configuration of the biological observation system 1 according to the first embodiment.

As shown in FIG. 6, the control section 223A is configured by including a table storage section 223a, a candidate vector calculation section 223b, an electromotive voltage error decision section 223f, an image generation section 223g, selectors 223i and 223j, an electromotive voltage error calculation section 223k, and a selector control section 223s. Furthermore, the control section 223A is configured to be able to perform control on the drive signal transmitting section 221 associated with the output of drive signals to the source coils C1 to Cn. Through such control of the control section 223A, the drive signal transmitting section 221 outputs drive signals so as to drive, for example, the source coils C1 to Cn one by one.

The selector 223i is configured to be able to select a magnetic field detection signal outputted from one of coil groups 211 to 214 and output the magnetic field detection signal to the candidate vector calculation section 223b based on the control of the selector control section 223s.

The selector 223j is configured to be able to select a magnetic field detection signal outputted from one of coil groups 211 to 214 and output the magnetic field detection signal to the electromotive voltage error calculation section 223k based on the control of the selector control section 223s.

The electromotive voltage error calculation section 223k reads the same coordinate data tq read by the candidate vector calculation section 223b from among the pieces of respective coordinate data included in the table data 223h of the table storage section 223a. After that, the electromotive voltage error calculation section 223k calculates an estimated electromotive voltage corresponding to the coordinate data tq based on the coordinate data tq read from the table storage section 223a, and the calculation result of the candidate vector outputted from the candidate vector calculation section 223b. The electromotive voltage error calculation section 223k calculates electromotive voltage errors $\Delta vx$, $\Delta vy$ and $\Delta vz$ which are differences between voltages (signal levels) of the magnetic field detection signal outputted via the magnetic field detection signal receiving section 222 and the selector 223j and the aforementioned estimated electromotive voltage and outputs the calculation result to the electromotive voltage error decision section 223f.

The selector control section 223s performs control for setting a path associated with input/output of magnetic field detection signals in the selectors 223i and 223j to an appropriate path while monitoring, as required, the situation in which calculations are performed in the candidate vector calculation section 223b, the electromotive voltage error decision section 223f and the electromotive voltage error calculation section 223k. Details of such control will be described later.

Next, the operation of the present embodiment will be described. Hereinafter, parts associated with the operation and processing or the like of the endoscope shape detection apparatus 3 provided with the control section 223A instead of the control section 223 will be described with reference to the flowchart in FIG. 7 and the other parts will be omitted as appropriate. Furthermore, hereinafter, for simplicity of description, a case will be described as an example where magnetic fields emitted from the respective source coils are detected in order of the source coils C1, C2, . . . , Cn and magnetic field detection signals are outputted in the same order.

When a magnetic field is emitted from the source coil Cp, a magnetic field detection signal corresponding to the magnetic field is outputted from each coil of the coil groups 211, 212, 213 and 214 (step S101 in FIG. 7).

On the other hand, the selector control section 223s performs control of setting the path of the selector 223i so that a magnetic field detection signal outputted from one of the coil groups 211 to 214 is inputted to the candidate vector calculation section 223b based on the situation in which calculations are performed in the candidate vector calculation section 223b, the electromotive voltage error decision section 223f and the electromotive voltage error calculation section 223k and setting of the path of the selector 223j so that magnetic field detection signals outputted from the other three coil groups other than the one coil group are sequentially inputted to the electromotive voltage error calculation section 223k (step S102 in FIG. 7).

To be more specific, the selector control section 223s performs control of setting the path of the selector 223i so that, for example, the magnetic field detection signal outputted from the coil group 211 is inputted to the candidate vector calculation section 223b, and setting the path of selector 223j so that the magnetic field detection signals outputted from the coil groups 212 to 214 are sequentially inputted to the electromotive voltage error calculation section 223k.

The present embodiment is not limited to the configuration in which the path of the selector 223j is set so that the magnetic field detection signals from the aforementioned three other coil groups are sequentially inputted to the electromotive voltage error calculation section 223k, but may also have a configuration in which the path of the selector 223j is set so that the magnetic field detection signals are simultaneously inputted to the electromotive voltage error calculation section 223k.

The candidate vector calculation section 223b reads the coordinate data tq from the respective coordinate data included in the table data 223h of the table storage section 223a. After that, the candidate vector calculation section 223b calculates a candidate vector corresponding to the coordinate data tq based on the coordinate data tq read from the table storage section 223a and the voltage (signal level) of the magnetic field detection signal outputted via the selector 223i (step S103 in FIG. 7), and outputs the calculation result to the electromotive voltage error calculation section 223k.

The electromotive voltage error calculation section 223k reads the same coordinate data tq read by the candidate vector calculation section 223b from the respective coordinate data included in table data 223h of the table storage section 223a. After that, the electromotive voltage error calculation section 223k calculates an estimated electromotive voltage corresponding to the coordinate data tq based on the coordinate data tq read from the table storage section 223a and the calculation result of the candidate vector outputted from the candidate vector calculation section 223b (step S104 in FIG. 7).

Furthermore, the electromotive voltage error calculation section 223k calculates electromotive voltage errors Δvx, Δvy and Δvz which are differences between voltages (signal levels) of the magnetic field detection signals outputted via the selector 223j and the aforementioned estimated electromotive voltage for each of the aforementioned other three coil groups (step S105 in FIG. 7), adds up nine electromotive voltage errors obtained as calculation results (step S106 in FIG. 7), and then stores and retains the addition value obtained in a memory provided for itself (not shown) as the addition result.

Upon detecting that the addition value has been calculated based on the situation in which calculations are performed in the candidate vector calculation section 223b, the electromotive voltage error decision section 223f and the electromotive voltage error calculation section 223k, the selector control section 223s decides whether or not the magnetic field detection signals of all the coil groups (coil groups 211 to 214) have already been inputted to the candidate vector calculation section 223b (step S107 in FIG. 7). When there is a coil group which has not inputted magnetic field detection signals, the selector control section 223s returns to step S102 in FIG. 7 and resets the paths in the selectors 223i and 223j so that magnetic field detection signals from the coil group is inputted to the candidate vector calculation section 223b. Furthermore, when magnetic field detection signals of all the coil groups have been inputted to the candidate vector calculation section 223b, the selector control section 223s outputs a completion signal indicating that fact to the electromotive voltage error calculation section 223k.

That is, according to the present embodiment, in the meantime until the aforementioned completion signal is outputted from the selector control section 223s, the processes in step S102 to S107 in FIG. 7 are repeated and the addition value of electromotive voltage errors in accordance with a candidate vector calculated for each coil group is stored in the memory of the electromotive voltage error calculation section 223k. Upon detecting the input of the aforementioned completion signal, the electromotive voltage error calculation section 223k outputs all addition values (four types of addition values) stored in the memory of the electromotive voltage error calculation section 223k to the electromotive voltage error decision section 223f and then resets the memory.

The electromotive voltage error decision section 223f applies addition processing to the four types of addition values outputted from the electromotive voltage error calculation section 223k corresponding to all the electromotive voltage errors for the coordinate data tq (step S108 in FIG. 7). Almost simultaneously with such addition processing, the electromotive voltage error decision section 223f reads the same coordinate data tq read by the candidate vector calculation section 223b.

After that, the electromotive voltage error decision section 223f decides whether or not the addition processing results of all electromotive voltage errors corresponding to the coordinate data tq are a minimum with respect to the addition processing results of electromotive voltage errors obtained earlier (step S109 in FIG. 7). Upon deciding that the addition processing result of the electromotive voltage errors corresponding to the coordinate data tq is a minimum, the electromotive voltage error decision section 223f updates the maximum likelihood position information in accordance with the addition processing result (step S110 in FIG. 7) and then moves to the processing in step S112 in FIG. 7. Furthermore, upon deciding that the addition processing result of electromotive voltage errors corresponding to the coordinate data tq is not a minimum, the electromotive voltage error decision section 223f discards the addition processing result and moves to the processing in step S112 in FIG. 7 while maintaining the maximum likelihood position information obtained earlier (step S111 in FIG. 7).

The aforementioned maximum likelihood position information is information stored in the memory (not shown) provided for electromotive voltage error decision section 223f and contains the addition processing result when the addition processing result of electromotive voltage error becomes a minimum value and one piece of coordinate data associated with the addition processing result. That is, the decision processing in step S109 in FIG. 7 is performed by comparing the addition processing result obtained by reading the maximum likelihood position information stored in the memory of the electromotive voltage error decision section 223f with the addition processing result of electromotive voltage errors obtained in step S108 in FIG. 7. According to the processing result of such decision processing, the maximum likelihood position information stored in the memory of the electromotive voltage error decision section 223f is rewritten as appropriate. However, when q=1, since there is no earlier maximum likelihood position information, the process moves to step S110 without performing the decision processing in step S109 in FIG. 7, and the addition processing result of electromotive voltage errors obtained in step S108 and the coordinate data t1 associated with the addition processing result are stored in the aforementioned memory as maximum likelihood position information.

On the other hand, when the above-described sections of the control section 223A have not completed the processing on all the coordinate data t1 to tm (step S112 in FIG. 7), after the next coordinate data t(q+1) is read (step S113 in FIG. 7), the processes in step S102 to step S111 in FIG. 7 are performed using the coordinate data t(q+1). Furthermore, when the processing on all the coordinate data t1 to tm is completed (step S112 in FIG. 7), the electromotive voltage error decision section 223f acquires the coordinate data contained in the maximum likelihood position information retained in itself at that point as the estimated position of the source coil Cp (step S114 in FIG. 7).

When the estimated positions of all the source coils C1 to Cn are not obtained (step S115 in FIG. 7), the processes in step S101 to step S114 in FIG. 7 are performed based on the magnetic field detection signal in accordance with the magnetic field emitted from the next source coil C(p+1) (step S115 in FIG. 7). On the other hand, when the estimated positions of all the source coils C1 to Cn are obtained, the electromotive voltage error decision section 223f outputs the information on the estimated positions of the source coils C1 to Cn to the image generation section 223g.

The image generation section 223g generates a shape detection image showing the shape of the insertion portion 11 based on the estimated positions of the source coils C1 to Cn outputted from the electromotive voltage error decision section 223f. Furthermore, the image generation section 223g sets the display position so that the side of the shape detection image closest to the root (proximal end side) is displayed at the center of the bottom in the display screen of the display 23 based on the reference position specified by the reference position specification apparatus 24. The image generation section 223g then generates a video signal based on the shape detection image whose display position is set and outputs the video signal to the display 23.

As described so far, according to the present embodiment, it is possible to obtain an estimated position of each source coil without performing calculation using the orientation of the source coil as a variable. For this reason, according to the present embodiment, it is possible to reduce the amount of calculation when obtaining the estimated positions of the source coils, that is, shorten the time required to detect the shape of the probe inserted in the subject compared to the conventional art.

Furthermore, according to the present embodiment, it is possible to obtain effects substantially similar to those of the first embodiment in the aspects of improvement of responsivity to the insertion operation (and removing operation) of the insertion portion and improvement of the image quality of the shape detection image.

On the other hand, as described so far, the present embodiment is configured to perform calculation to obtain the orientation of the source coil for each coil group provided for the sensing coil unit. For this reason, according to the present embodiment, it is possible to obtain estimated positions of the source coils with high accuracy while reducing the amount of calculation.

Here, according to the above-described embodiments, deviation correction processing may further be performed to correct a deviation in the display position of the shape detection image generated as the subject lying on his/her side on the inspection bed moves.

To be more specific, the aforementioned deviation correction processing can be realized by incorporating processing of detecting an extent to which the display position of the side of the shape detection image closest to the root (proximal end side) is deviated from the center of the bottom in the display screen of the display and horizontally moving the shape detection image in accordance with the detection result as part of the processing of the image generation section 223g.

Figure 8:
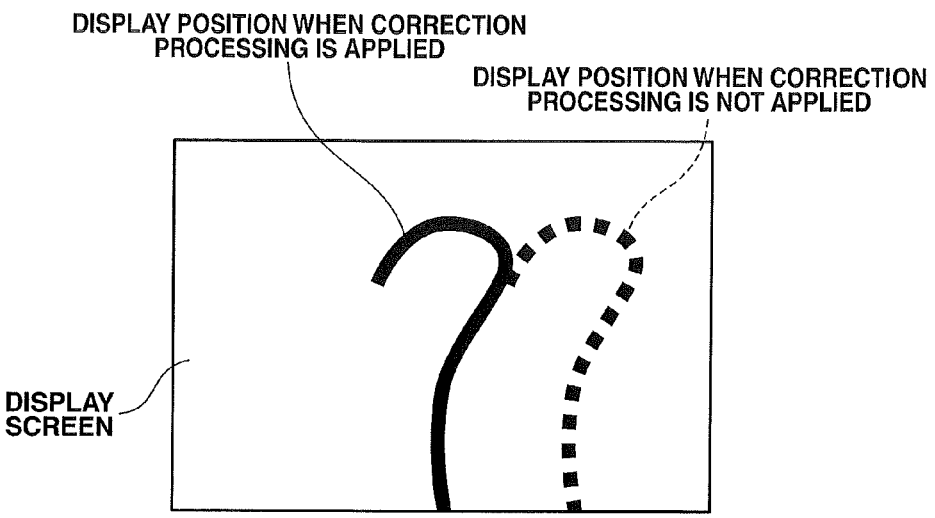
FIG. 8 is a diagram illustrating processing of correcting a deviation of a display position of a shape detection image.

By performing the aforementioned deviation correction processing, it is possible to display the shape detection image at an easy-to-see position in the display screen of the displays as shown in FIG. 8.

Furthermore, according to the aforementioned embodiments, information on the insertion state or the like of the insertion portion may be displayed together with the shape detection image.

Figure 9:
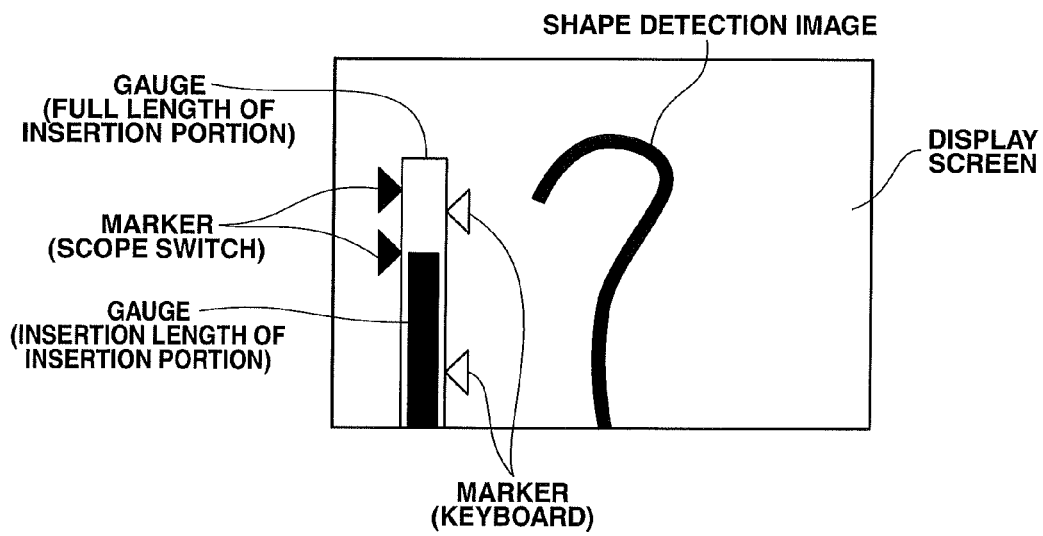
FIG. 9 is a diagram illustrating a case where information on an insertion condition of the insertion portion or the like is displayed together with the shape detection image.

To be more specific, this can be realized by incorporating the processing of displaying, for example, a gauge for indicating the full length and the insertion length of the insertion portion as shown in FIG. 9 next to the shape detection image as part of the processing of the image generation section 223g.

In FIG. 9, markers that can identify a position (insertion length) at which a predetermined switch of the scope switch is operated and a position (insertion length) at which a predetermined key of the keyboard is operated are displayed together. The processing associated with the display of such markers can also be realized by incorporating the processing as part of the image generation section 223g as in the case of the processing associated with the display of the gauge indicating the full length and the insertion length of the insertion portion.

Furthermore, according to the above-described embodiments, inclination correction processing may further be performed for correcting a variation in the display shape of the shape detection image caused by an inclination of the sensing coil unit.

To be more specific, the aforementioned inclination correction processing can be realized by incorporating processing of, for example, detecting an angle of inclination of the sensing coil unit (with respect to the vertical direction) based on a detection signal from an acceleration sensor (inclination sensor) provided in the sensing coil unit and modifying and (or) moving the shape detection image according to the detection result as part of the processing of the image generation section 223g.

Figure 10:
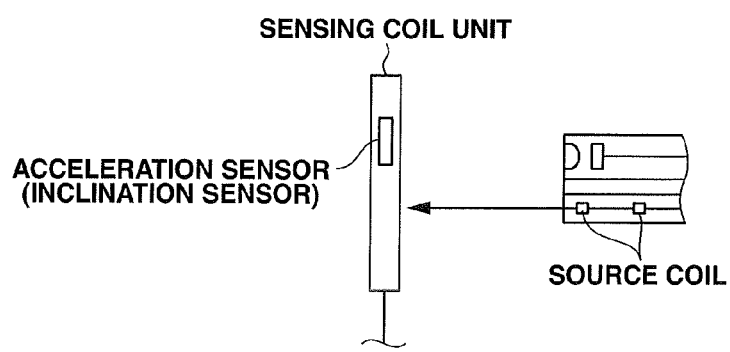
FIG. 10 is a diagram illustrating an example of a position relationship between a source coil and the sensing coil unit.
Figure 11:
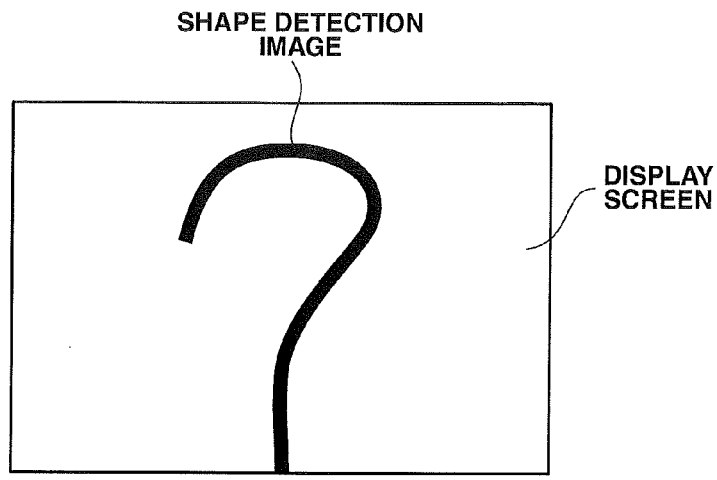
FIG. 11 is a diagram illustrating an example of the shape detection image displayed on a display screen of a display.
Figure 12:
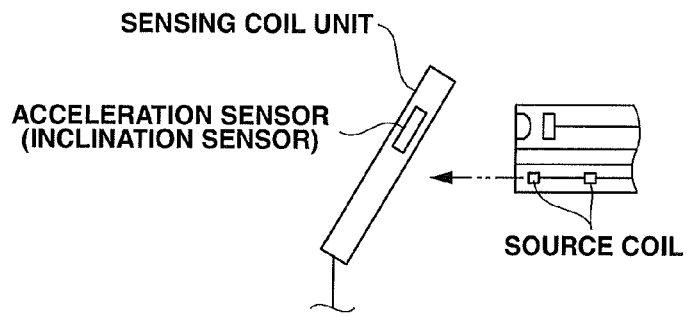
FIG. 12 is a diagram illustrating a position relationship between the source coil and the sensing coil unit different from FIG. 10.
Figure 13:
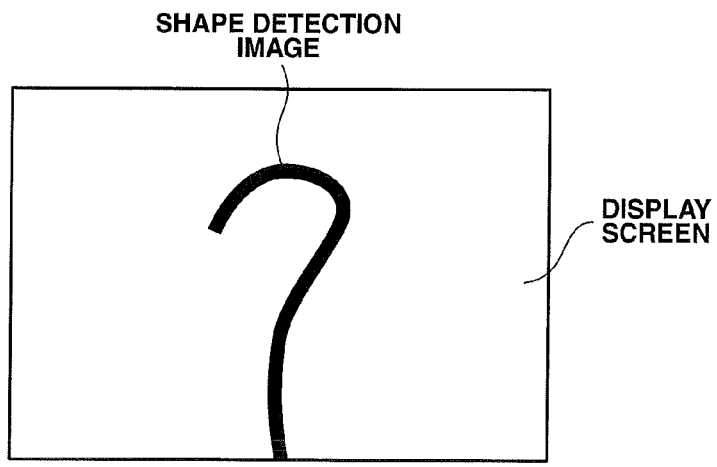
FIG. 13 is a diagram illustrating the shape detection image displayed on the display screen of the display different from FIG. 11.

Here, when a magnetic field from the source coil is detected with the sensing coil unit not being inclined toward the source coil (e.g., in a positional relationship shown in FIG. 10), a shape detection image having a shape shown in FIG. 11 is displayed. On the other hand, when a magnetic field from the source coil is detected with the sensing coil unit being inclined toward the source coil (e.g., in a positional relationship shown in FIG. 12), there is conventionally a problem that the display shape of the shape detection image is changed from the one shown in FIG. 11 to the one shown in FIG. 13 although the insertion portion is not moved at all.

That is, the aforementioned inclination correction processing is implemented to solve such a problem and is processing intended to always display, even if the sensing coil unit is inclined with respect to the vertical direction, a shape detection image having the same shape as that when the sensing coil unit is not inclined with respect to the vertical direction as long as the position of the source coil is not changed.

The present invention is not limited to the aforementioned embodiments, but it goes without saying that various modifications or applications can be made thereto without departing from the spirit and scope of the invention.

What is claimed is:

1. A probe shape detection apparatus comprising:
a drive signal transmitting section that transmits a drive signal for causing a magnetic field to be generated from a magnetic field generation element provided along a longitudinal direction of a probe having an elongated shape;

a first magnetic field detection section that detects the magnetic field emitted from the magnetic field generation element as magnetic field components in three mutually orthogonal axial directions and outputs a magnetic field detection signal corresponding to a first electromotive voltage group generated when detecting the magnetic field components in the three axial directions;

a second magnetic field detection section provided at a position different from the first magnetic field detection section that detects the magnetic field emitted from the magnetic field generation element as magnetic field components in the three axial directions and outputs a magnetic field detection signal corresponding to a second electromotive voltage group generated when detecting the magnetic field components in the three axial directions;

a candidate position storage section that stores a plurality of pieces of candidate position information indicating candidate positions that can be taken by the magnetic field generation element;

a candidate vector calculation section that calculates candidate vectors indicating orientation of the magnetic field generation element when the magnetic field generation element is assumed to be located at a position corresponding to one piece of candidate position information based on the first electromotive voltage group and the one piece of candidate position information read from the candidate position storage section;

an estimated electromotive voltage calculation section that calculates an estimated electromotive voltage estimated to be generated when the magnetic field emitted from the magnetic field generation element is detected based on the one piece of candidate position information read from the candidate position storage section and the candidate vector calculated in the candidate vector calculation section;

an error calculation section that calculates an error between the second electromotive voltage group and the estimated electromotive voltage;

an estimated position acquiring section that acquires a candidate position where the error is minimized among all candidate positions indicated as the candidate position information based on the calculation result of the error calculation section as an estimated position of the magnetic field generation element; and an image generation section that generates a shape detection image showing the shape of the probe based on the respective estimated positions acquired in the estimated position acquiring section.

2. The probe shape detection apparatus according to claim 1, further comprising a third magnetic field detection section that is provided at a position different from the first magnetic field detection section and the second magnetic field detection section, detects a magnetic field emitted from the magnetic field generation element as magnetic field components in the three axial directions and outputs a magnetic field detection signal in accordance with a third electromotive voltage group generated when detecting the magnetic field components in the three axial directions, wherein the error calculation section calculates a first error which is an error between the second electromotive voltage group and the estimated electromotive voltage and a second error which is an error between the third electromotive voltage group and the estimated electromotive voltage, and the estimated position acquiring section acquires, based on an addition result obtained by adding up the first error and the second error, a candidate position that minimizes the addition result among all candidate positions indicated as the candidate position information, as an estimated position of the magnetic field generation element.

3. The probe shape detection apparatus according to claim 2, further comprising:

a first selector that can selectively cause one magnetic field detection signal outputted from one magnetic field detection section to be inputted, among the first magnetic field detection section, the second magnetic field detection section and the third magnetic field detection section to the candidate vector calculation section;

a second selector that can selectively cause two magnetic field detection signals outputted from the other magnetic field detection sections other than the one magnetic field detection section to be inputted, among the first magnetic field detection section, the second magnetic field detection section and the third magnetic field detection section to the error calculation section; and a selector control section that performs control for setting a path associated with input/output of magnetic field detection signals in the first selector and the second selector.

4. The probe shape detection apparatus according to claim 3, wherein the selector control section sets a path associated with input/output of magnetic field detection signals in the first selector and the second selector so that when the candidate vector calculation section reads the one piece of candidate position information and calculates the candidate vector, magnetic field detection signals from the first magnetic field detection section, the second magnetic field detection section and the third magnetic field detection section are inputted to the candidate vector calculation section one time each.

5. The probe shape detection apparatus according to claim 4, wherein the candidate vector calculation section calculates the candidate vector based on one electromotive voltage group in accordance with the one magnetic field detection signal outputted via the first selector and the one piece of candidate position information, the error calculation section calculates an error between the respective electromotive voltage groups in accordance with the two magnetic field detection signals outputted via the second selector and the estimated electromotive voltage, and the estimated position acquiring section acquires a candidate position that minimizes the addition result of all candidate positions shown as the candidate position information based on an addition result obtained by adding up the respective errors calculated in the error calculation section as an estimated position of the magnetic field generation element.

6. The probe shape detection apparatus according to claim 1, wherein the candidate vector calculation section, the estimated electromotive voltage calculation section and the error calculation section perform reading and processing only on either candidate position information within a predetermined range relative to an estimated position of the magnetic field generation element acquired last time or candidate position information within a range calculated using an estimated position of the magnetic field generation element acquired last time, of the respective candidate position information stored in the candidate position storage section.

7. A method of operating a probe shape detection apparatus, the method comprising:
- a drive signal transmitting step of a drive signal transmitting section transmitting a drive signal for causing a magnetic field generated from a magnetic field generation element provided along a longitudinal direction of a probe having an elongated shape;
- a first magnetic field detecting step of a first magnetic field detection section detecting the magnetic field emitted from the magnetic field generation element as magnetic field components in three mutually orthogonal axial directions and outputting a magnetic field detection signal corresponding to a first electromotive voltage group generated when detecting the magnetic field components in the three axial directions;
- a second magnetic field detecting step of a second magnetic field detection section detecting the magnetic field emitted from the magnetic field generation element as magnetic field components in the three axial directions and outputting a magnetic field detection signal corresponding to a second electromotive voltage group generated when detecting the magnetic field components in the three axial directions;
- a candidate vector calculating step of a candidate vector calculation section calculating candidate vectors indicating orientation of the magnetic field generation element when the magnetic field generation element is assumed to be located at a position corresponding to one piece of candidate position information based on the first electromotive voltage group and the one piece of candidate position information read from a candidate position storage section that stores a plurality of pieces of candidate position information indicating candidate positions that can be taken by the magnetic field generation element;
- an estimated electromotive voltage calculating step of an estimated electromotive voltage calculation section calculating an estimated electromotive voltage estimated to be generated when the magnetic field emitted from the magnetic field generation element is detected based on the one piece of candidate position information read from the candidate position storage section and the candidate vector calculated in the candidate vector calculating step;
- an error calculating step of an error calculation section calculating an error between the second electromotive voltage group and the estimated electromotive voltage;
- an estimated position acquiring step of an estimated position acquiring section acquiring a candidate position where the error is minimized among all candidate positions indicated as the candidate position information based on the calculation result of the error calculating step as an estimated position of the magnetic field generation element; and
- an image generating step of an image generation section generating a shape detection image showing a shape of the probe based on the respective estimated positions acquired in the estimated position acquiring step.

8. The method of operating a probe shape detection apparatus according to claim 7, further comprising a third magnetic field detecting step of a third magnetic field detection section detecting a magnetic field emitted from the magnetic field generation element as magnetic field components in the three axial directions and outputting a magnetic field detection signal in accordance with a third electromotive voltage group generated when detecting magnetic field components in the three axial directions,
- wherein in the error calculating step, a first error which is an error between the second electromotive voltage group and the estimated electromotive voltage and a second error which is an error between the third electromotive voltage group and the estimated electromotive voltage are calculated respectively, and
- in the estimated position acquiring step, based on an addition result obtained by adding up the first error and the second error, a candidate position that minimizes the addition result among all candidate positions indicated as the candidate position information is acquired as an estimated position of the magnetic field generation element.

9. The method of operating a probe shape detection apparatus according to claim 7, wherein the processes in the candidate vector calculating step, the estimated electromotive voltage calculating step and the error calculating step are performed on only any one of candidate position information within a predetermined range relative to the estimated position of the magnetic field generation element acquired last time and candidate position information within a range calculated using the estimated position of the magnetic field generation element acquired last time of the respective candidate position information stored in the candidate position storage section.

* * * * *